(12) United States Patent
Demmer et al.

(10) Patent No.: US 7,311,832 B2
(45) Date of Patent: Dec. 25, 2007

(54) ADSORPTION MEMBRANES, METHOD OF PRODUCING SAME AND EQUIPMENT, INCLUDING THE ADSORPTION MEMBRANES

(75) Inventors: Wolfgang Demmer, Goettingen (DE); Stefan Fischer-Fruehholz, Bovenden (DE); Andreas Kocourek, Hannover (DE); Dietmar Nussbaumer, Goettingen (DE); Eberhard Wuenn, Goettingen (DE)

(73) Assignee: Sartorius Stedim Biotech GmbH, Gottingen (DE)

( * ) Notice: Subject to any disclaimer, the term of this patent is extended or adjusted under 35 U.S.C. 154(b) by 360 days.

(21) Appl. No.: 10/949,305

(22) Filed: Sep. 27, 2004

(65) Prior Publication Data

US 2005/0115890 A1 Jun. 2, 2005

(30) Foreign Application Priority Data

Sep. 26, 2003 (DE) .................. 103 44 820

(51) Int. Cl.
*B01D 39/00* (2006.01)
*B01D 71/06* (2006.01)
*B01D 63/00* (2006.01)

(52) U.S. Cl. .................. 210/502.1; 210/500.27; 210/506; 210/500.22; 427/245; 427/246; 435/6; 422/101

(58) Field of Classification Search ............ None
See application file for complete search history.

(56) References Cited

U.S. PATENT DOCUMENTS

| | | | | |
|---|---|---|---|---|
| 3,862,030 A | * | 1/1975 | Goldberg | 210/767 |
| 3,888,771 A | * | 6/1975 | Isuge et al. | 210/500.23 |
| 4,102,746 A | * | 7/1978 | Goldberg | 435/96 |
| 4,373,519 A | * | 2/1983 | Errede et al. | 602/43 |
| 4,810,381 A | * | 3/1989 | Hagen et al. | 210/502.1 |
| 5,310,688 A | * | 5/1994 | Zale et al. | 436/535 |
| 5,891,649 A | * | 4/1999 | Kidwell et al. | 435/7.9 |
| 6,045,697 A | * | 4/2000 | Girot et al. | 210/635 |
| 6,048,457 A | * | 4/2000 | Kopaciewicz et al. | 210/321.6 |
| 6,383,783 B1 | * | 5/2002 | Haddad | 435/91.1 |
| 6,527,955 B1 | * | 3/2003 | Sun | 429/247 |
| 6,911,148 B1 | * | 6/2005 | Demmer et al. | 210/321.84 |
| 2002/0066699 A1 | * | 6/2002 | Boggs et al. | 210/483 |
| 2003/0006190 A1 | * | 1/2003 | Arnold et al. | 210/638 |

* cited by examiner

*Primary Examiner*—Krishnan S. Menon
(74) *Attorney, Agent, or Firm*—Sughrue Mion, Pllc.

(57) ABSTRACT

The present invention relates to adsorption membranes comprising microporous polymer membranes in which adsorbent particles are incorporated. Furthermore, the present invention relates to a method of producing the inventive adsorption membranes as well as devices which comprise the inventive adsorption membranes.

15 Claims, 4 Drawing Sheets

ADSORPTION MEMBRANES, METHOD OF PRODUCING SAME AND EQUIPMENT, INCLUDING THE ADSORPTION MEMBRANES

FIELD AND BACKGROUND OF THE INVENTION

The present invention relates to adsorption membranes, including microporous polymer membranes with particles of adsorbent embedded in them. Furthermore, the present invention also relates to a method of producing the inventive adsorption membranes as well as devices which include the adsorption membranes.

In the past, a variety of analytical methods have been developed which necessitate removing various substances such as solvents, low molecular ions and impurities from solutions such as peptide solutions which contain macromolecules in order to obtain sufficiently concentrated and purified samples for the respective analysis. Because of the sensitivity of these analytical methods, even small quantities of the aforementioned secondary constituents present in a sample to be analyzed can have a very negative effect on the analytical results.

One possibility of performing the separation described above is by adsorption, where components of a fluid, which may be individual molecules, associates or particles, are bound to the surface of a solid that is brought in contact with the fluid. A solid that is capable of adsorption is called an adsorbent, while the component to be adsorbed is called the adsorbate. Adsorption can be used technically for "adsorptive separation of substances," which is performed in equipment known as adsorbers. An adsorbent with a high percentage of coarse pores running through it is also known as a "perfusion matrix."

The adsorbate is known as the "target substance" when the goal is to recover it from the fluid, but it is called a "contaminant" when it is to be removed from the fluid. In the first case, the adsorption must be reversible, and adsorption is followed as the second process step by "elution" of the adsorbate under altered conditions (composition and/or temperature of the fluid). A target substance may be present as the only component in the fluid, so that the substance separation consists of a simple increase in concentration, or there may be multiple components which are to be separated. In this case, at least one of the two process steps must be "selective," i.e., must take place to a different extent for each of the components to be separated. If the fluid is a liquid, adsorptive separation of substances (not including gas chromatography) is also referred to as chromatography and the fluid is known as the medium. The mass of the adsorbate bound in equilibrium is known as "static capacity," based on the unit of mass of the adsorbent. Its dependence on the concentration of the adsorbate in the fluid is described by the adsorption isotherms. The specific surface area of an adsorbent is also critical in determining its capacity, which is why adsorbents preferably have a high porosity. A distinction is made between "external specific surface", i.e., the geometric surface/mass ratio, and the "internal specific surface", i.e. the pore surface/mass ratio. The prerequisite for the bonding availability of the internal surface is its steric accessibility for the adsorbate, i.e., its "exclusion limit" which is characterized in the case of chromatography, for example, by the molecular weight of globular proteins which just can no longer penetrate into the pores.

Adsorption ability may be inherent in a solid substance, e.g., in the case of activated carbon and hydroxyl apatite, or it may be achieved by "adsorptive modification" of a "base material," i.e., a preferably adsorptively inert solid having a suitable morphology, consisting of covalent bonding of chemical units to superficial "anchor groups" of the base material, these chemical units being referred to as "ligands" which are preferably capable of selective bonding.

With the porous solids considered for use as base materials, a distinction is made between aerogels and xerogels, the former being characterized by a rigid structure which may also have continuous pores, and in most cases a high mechanical strength, which can be promoted in particular by a crystalline structure and whose pore sizes are usually directly accessible by measurement technology, including the BET method, while xerogels usually consist of crosslinked chains of a polymer that is originally soluble in the medium.

There is a large selection of particulate base materials with particle sizes between about 1 μm and several mm, including silica gels (silicon dioxide gels), porous glass, cellulose and organic polymers based on methacrylate and styrene as traditional aerogels, those which approach aerogels and in particular agarose gels as well as dextran gels, polyacrylamide gels and other synthetic polymer gels as traditional xerogels. In addition, there are composite gels in many combinations, where a xerogel is incorporated into the pores of an aerogel.

However, there are a number of disadvantages when such base materials are used to produce an adsorbent:

1. Loading of an adsorber with the corresponding adsorbent is complicated because irregularities, channeling and the like must be prevented. There are also unavoidable deleterious edge effects between the adsorbent and the adsorber housing.

2. There is an antagonism between the pressure drop and the transport kinetics such that the latter is facilitated by smaller particle sizes but the pressure drop is increased at the same time. Particles down to 1 μm in diameter, optionally even in a nonporous form, are therefore above all used for analytical separations in so-called HPLC (high performance liquid chromatography). For applications on an industrial scale, however, relatively large particles must be used in order to limit the pressure drop. The unfavorable transport kinetics in this case can be improved only slightly by using particulate perfusion matrices. In addition, a low pressure drop can be achieved only with approximately monodisperse spherical particles but these are much more expensive to produce in comparison with irregularly shaped particles.

Accordingly attempts have been made to avoid the disadvantages described above by using non-particulate adsorbents. The non-particulate adsorbents which have gained wide acceptance in practice are mainly in the form of compact bodies which are always perfusion matrices and flat configurations. A compact adsorbent is described in U.S. Pat. No. 6,048,457, the object of which is adsorbent bodies produced in situ in pipette tips, said adsorbent bodies consisting of particles of an adsorbent embedded in a porous polymer matrix. However, the production process does not offer good scale-up opportunities any better than those proposed by Svec (T. B. Tennikova et al., *Journal of Chromatography*, 555, (1991), pages 97 to 107) based on polymerization of ethylenically unsaturated monomers to form structures of a suitable shape and porosity. This latter process is limited by the impossibility of removing the reaction heat generated with larger units.

Flat adsorbents have a thickness of approximately 10 to 1,000 µm and can be processed to yield adsorbers of the desired dimensions. When they are perfusion matrices, they are called "adsorption membranes." The traditional "filtration membranes" may be used as the base materials. These are flat aerogel sheets having average pore sizes from approximately 0.05 µm to 10 µm; they are referred to as asymmetrical when they have a pore size gradient over the thickness. Symmetrical however refers to membranes that do not have a pore size gradient over the thickness. The filtration membranes may come in different forms, e.g., flat membranes, hollow fiber membranes or tubular membranes. Filtration membranes, however, have the following disadvantages for adsorptive modification:

1. Most of the polymers suitable for producing them such as polysulfones, polyvinyl chloride (PVC), etc. do not have an adequate density of suitable anchor groups and they have a rather marked tendency to nonspecific adsorption.

2. In the pore size range which ensures a high hydraulic permeability, there is not a sufficient specific surface area to achieve high capacities.

3. The chemical conversion of sheet materials necessitates mechanically complex equipment for technical implementation and requires the use of large volumes of reaction media.

Adsorption membranes are available commercially under the name Acti-Disc (brand name of FMC Corporation, Philadelphia, and later Arbor Technologies, Inc., Ann Arbor, Mich.). These membranes are produced from the membranes described in U.S. Pat. No. 3,862,030 according to the company brochure B405 of Arbor Technologies, Inc. This membrane consists of a synthetic polymer having pores varying irregularly in the size range from 0.01 µm to 100 µm distributed irregularly over its thickness and containing particles. In the manner of a deep bed filter, it is impermeable for particles smaller than the largest pores, so it should even be suitable as a sterile filter. It follows from this that they become clogged sooner or later due to the particulate impurities that are always present in real media when these membranes are used in membrane chromatography, and this blockage cannot be reversed even by reversing the direction of flow ("backwashing"). Furthermore, the silica gel particles whose adsorptive properties have been modified according to the company brochure mentioned above and which are used in the membrane are not porous, which results in a low adsorption capacity. With regard to the production process, reference is made in the company brochure to U.S. Pat. No. 4,102,746, in which adsorptive modification of the particles is performed subsequently, i.e., when they are already in the membrane sheet. As with the product mentioned above, this has the abovementioned disadvantages of chemical reactions on the membrane sheet.

Membranes containing particles are also used in a variety of applications in the medical field. For example, U.S. Pat. No. 4,373,519 proposes the use of PTFE membranes containing dextran particles for wound closure but they are not suitable as adsorption membranes because of their lack of adsorption capacity. United States Patent Application A-2002/0,066,699 discloses a membrane consisting of a polymer matrix and adsorptive particles immobilized in the matrix. The membrane has a selectively permeable skin which is provided with openings at irregular intervals on both sides and is capable of remaining organic compounds from a biological fluid. The skin should prevent the penetration of its shaped constituents into the membrane matrix in the intended use of the membrane, namely static adsorption of chemicals from blood. The presence of a skin, in particular when it has large openings, is a disadvantage in adsorption membranes because in those areas where the skin occurs, the hydraulic permeability is reduced, whereas it is not reduced in the area of the openings. This results in irregular flow velocities through the membrane over the membrane area, which results in premature exhaustion of the adsorption capacity in regions of high hydraulic permeability and there is a flow-through of the adsorbate before exhausting the capacity of the entire membrane. U.S. Pat. No. 4,728,432 describes membranes containing adsorptive particles for use in an adsorber according to the principle of tangential separation of substances. In the preferred embodiments, the membrane contains a support with a network structure and has 40-45% free area which makes them unsuitable as an adsorption membrane for the same reasons as given above.

OBJECTS OF THE INVENTION

Therefore, the object of the present invention is to provide adsorption membranes having a high separation capacity with regard to samples that are to be purified and/or concentrated while avoiding the problems described above. Additional objects of the present invention include providing a method for producing the adsorption membranes and equipment, including said adsorption membranes.

SUMMARY OF THE INVENTION

This object is achieved by the embodiments characterized in the claims.

In particular an adsorption membrane is made available, comprising a microporous polymer membrane having an essentially symmetrical pore structure, with adsorbent particles being incorporated into the pores, and with the adsorbent particles being arranged essentially uniformly over the entire cross section of the membrane and having either a spherical shape or an irregular shape.

The inventive adsorption membrane has a thickness of 50 µm to 500 µm, preferably 100 µm to 250 µm and most preferably 125 µm to 180 µm. In addition, the inventive adsorption membrane has a symmetrical pore structure, so there is no pore size gradient over the thickness of the membrane. The maximum pore diameter here is 0.1 µm to 10 µm, more preferably 0.2 µm to 5 µm, most preferably 1 µm to 5 µm. This pore diameter can be determined by the BET method or by measurement with an electron microscope.

The adsorbent particles incorporated into the pores of the microporous polymer membrane have a diameter which is 5% to 80%, preferably 10% to 60%, most preferably 20% to 30% smaller than the maximum pore diameter. The adsorbent particles contained in the inventive adsorption membrane may be either monodisperse, i.e., all of them having essentially the same size, or they may have a continuous particle size distribution (from 0 to the stated values). The shape of the particles may be either spherical or irregular.

The adsorbent particles are arranged essentially uniformly in the microporous polymer membrane which is comprised by the inventive adsorption membrane, e.g., as shown in FIG. 2 for the case of monodisperse spherical particles. Accordingly, there is essentially no local accumulation of adsorbent particles in the cross section of the inventive adsorption membrane but instead there is a uniform distribution of the adsorbent particles in the pores over the entire membrane area, with the density of the adsorbent particles in the inventive adsorption membrane being dependent upon the volume fraction of the particles in the microporous polymer membrane.

The adsorbent particles contained in the inventive adsorption membrane may be inherently adsorptive as in the case of activated carbon and hydroxyl apatite or they may be achieved by adsorptive modification of a porous or nonporous base material, a preferably adsorptively inert solid of a suitable morphology. This consists of the fact that chemical units known as ligands, which are capable of preferably selective bonding, are covalently bonded to superficial anchor groups of the solid.

The choice of particulate base materials for the adsorbent particles of the inventive adsorption membrane includes, for example, silica gels, porous glass, cellulose and/or organic polymers based on methacrylate and styrene as traditional aerogels, gels resembling aerogels and in particular agarose gels as well as dextran gels, polyacrylamide gels and other synthetic polymer gels as traditional xerogels. In addition there are composite gels in suitable combinations, where a xerogel is incorporated into the pores of an aerogel.

Porous silica particles modified with hydrocarbon ligands with 2 to 24 carbon atoms, in particular $C_{18}$ ligands, as well as agarose particles modified with ligands capable of specific interaction with biomolecules are especially preferred as the adsorbent particles of the inventive adsorption membrane. Examples of ligands interacting with the adsorbate(s) include ion exchangers, chelating agents and heavy metal chelates, thiophilic, hydrophobic ligands of various chain lengths and configurations, reversed phase systems, dye ligands, affinity ligands, amino acids, coenzymes, cofactors such as FAD and their analogs, substrates and their analogs, endocrine and exocrine substances such as hormones and agents that act like hormones, effectors and their analogs, enzyme substrates, enzyme inhibitors and their analogs, fatty acids, fatty acid derivatives, conjugated fatty acids and their analogs, nucleic acids such as DNA, RNA and their analogs and derivatives (single-stranded, double-stranded and/or multiple-stranded) as well as peptide nucleic acids and their derivatives, monomers and their analogs and derivatives, oligomers to polymers and their analogs and derivatives, high molecular carbohydrates which may be linear or branched, substituted or non-substituted, polymeric glyco conjugates such as heparin, amylose, cellulose, chitin, chitosan, as well as their monomers and oligomers and derivatives and analogs thereof, lignin and its derivatives and analogs, other biochemical ligands such as oligopeptides and polypeptides, e.g., proteins such as protein A, cytochrome c, IgG and ferritin and their oligomers, multimers, subunits and parts thereof, in particular lectins, antibodies, fusion proteins, haptens, enzymes and subunits as well as parts thereof, structural proteins, receptors and effectors as well as parts thereof, plus xenobiotics, pharmaceuticals and pharmaceutical active ingredients, alkaloids, antibiotics, biomimetics, etc.

Of the aforementioned ligands which are bound to agarose, protein A is preferred.

In the inventive adsorption membrane, the microporous polymer membrane includes at least one polymer selected from the group consisting of polysulfone, polyether sulfones, cellulose acetate, cellulose acetate butyrate, acrylonitrile/PVC copolymer, polyvinylidene fluoride, polystyrene, polystyrene/acrylonitrile copolymer, polyolefins and polyamides [nylon].

In addition, the amount of adsorbent particles by weight in the inventive membrane amounts to 1% to 70%, preferably 10% to 60% and most preferably 40% to 50%.

In addition, preferably between 10% and 80%, more preferably between 20% and 60% and most preferably between 30% and 40% of the pore volume of the microporous polymer membrane comprised by the adsorption membrane according to this invention should be filled with adsorbent particles.

The inventive adsorption membranes thus have relatively coarse continuous pores, which permit high hydraulic permeabilities as well as fine-pore regions which are in enclosed particulate porous adsorbents and ensure high capacities. The particulate adsorbents used may be perfusion matrices according to this invention to improve the kinetic properties and/or may have a very small size which has as little deleterious effect on their hydraulic permeability as does an irregular particle shape, which has the economic advantages mentioned above.

The present invention also relates to a method of producing an adsorption membrane comprising a microporous polymer membrane having an essentially symmetrical pore structure, with adsorbent particles incorporated into the pores, arranged essentially uniformly over the entire cross section of the membrane and having either a spherical shape or an irregular shape. The method includes the following steps:

(a) producing a polymer casting solution,
(b) introducing adsorbent particles into the polymer casting solution,
(c) converting the resulting solution to a membrane form,
(d) placing the shaped solution in a precipitation bath to perform a controlled phase reversal, forming a porous membrane filled with particles and
(e) removing the remaining solvent.

When using modified adsorbent particles such as porous silica particles with hydrocarbon ligands having 2 to 24 carbon atoms or agarose particles modified with biomolecules, the corresponding modification is preferably performed before introducing the corresponding adsorbent particles into the polymer casting solution in step (b) of the inventive method described above. This makes it possible to avoid modification of membrane materials that are already finished, entailing, for example, the use of mechanically complicated equipment and large volumes of reaction media and leading to inconsistent results. Surprisingly the introduction of previously modified adsorbent particles into the polymer casting solution and/or further processing of the resulting casting solution containing adsorbent particles in the inventive method for producing an absorption membrane does not lead to disadvantages such as a partial cleavage or decomposition of the ligands of the modified adsorbent particles.

In addition, in the inventive method for producing an adsorption membrane, measures may advantageously be taken so that the possibility of contact between the adsorbent particle surface area in a finished inventive adsorption membrane and the liquid to be treated, containing an adsorbate, for example, is not impaired after embedding the adsorbent particles in the membrane. This would be the case, for example, if essential parts of the adsorbent particle surface or its pore volume were blocked by the polymer carrier. This can be prevented to advantage in the inventive method by the fact that attractive forces are ruled out between these polymer molecules and the adsorbent particles in the stages of the production process in which the polymer molecules are freely mobile, and this is preferably achieved by the fact that the polymer molecules and the adsorbent particles have the same electric charges.

In the inventive method for producing an adsorption membrane, the controlled phase reversal is achieved through the targeted adjustment of the ratio of precipitation agent and solvent for the polymer used, with water being a conventional precipitation agent. This avoids a sudden phase reversal occurring when using a pure precipitation agent such as water, which would result in a skin being formed on the resulting membrane which would have only a few very small pores or none at all and an underlying asymmetrical pore structure is formed in the corresponding membrane. Accordingly, an adsorption membrane produced by the inventive method does not have any skin and it also has a symmetrical pore structure as illustrated in FIG. 2 and FIG. 3, for example.

In addition, the present invention provides an adsorber device comprising a housing which defines a volume, whereby the housing has a first open end and a second open end at a distance from the first open end. An inventive adsorption membrane is arranged in a section of the volume between the two ends. The housing of the inventive adsorber device may assume any shape. The inventive adsorption membrane may be cut to size accordingly, for example.

The adsorption membrane may also be arranged directly at one of the two ends of the housing in any form in the inventive adsorber device. Such an adsorber device as mentioned above may, according to this invention, have a housing which is designed, for example, so that it may be introduced into another container such as a centrifuge tube.

In addition, any number of inventive adsorber devices of the aforementioned type may be arranged side by side, e.g., in the form of a multiple microtiter plate.

BRIEF DESCRIPTION OF THE DRAWINGS

The invention will now be described with reference to the schematic figures in which.

Figure 1:
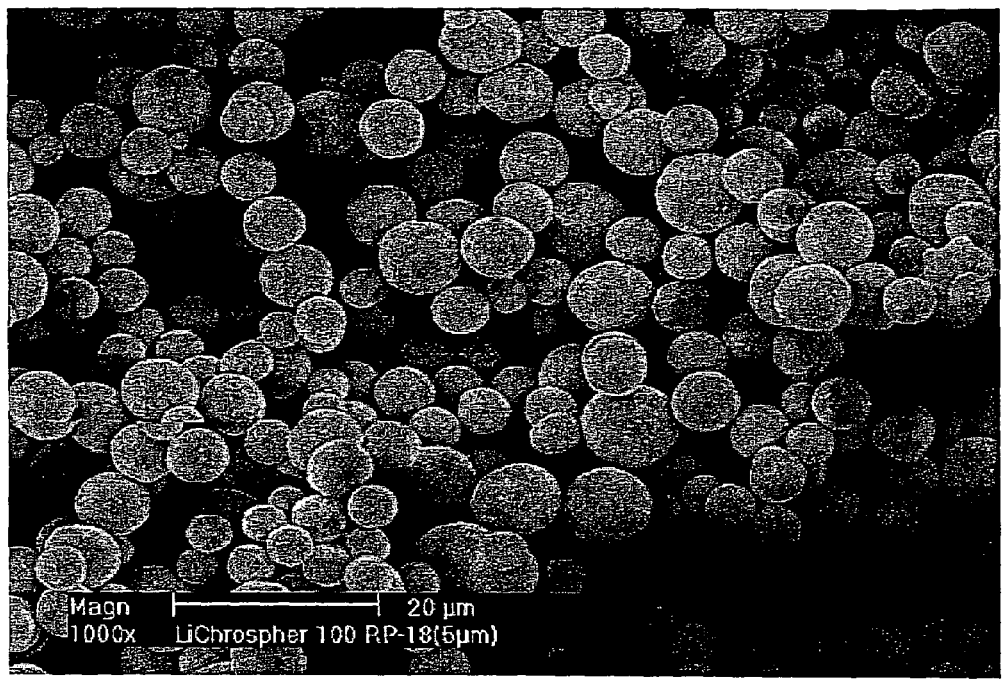
FIG. 1 shows a scanning electron micrograph of the silicon dioxide particles used in Example 10. These particles may be used, for example, as adsorbent particles in the inventive adsorption membrane.
Figure 2:
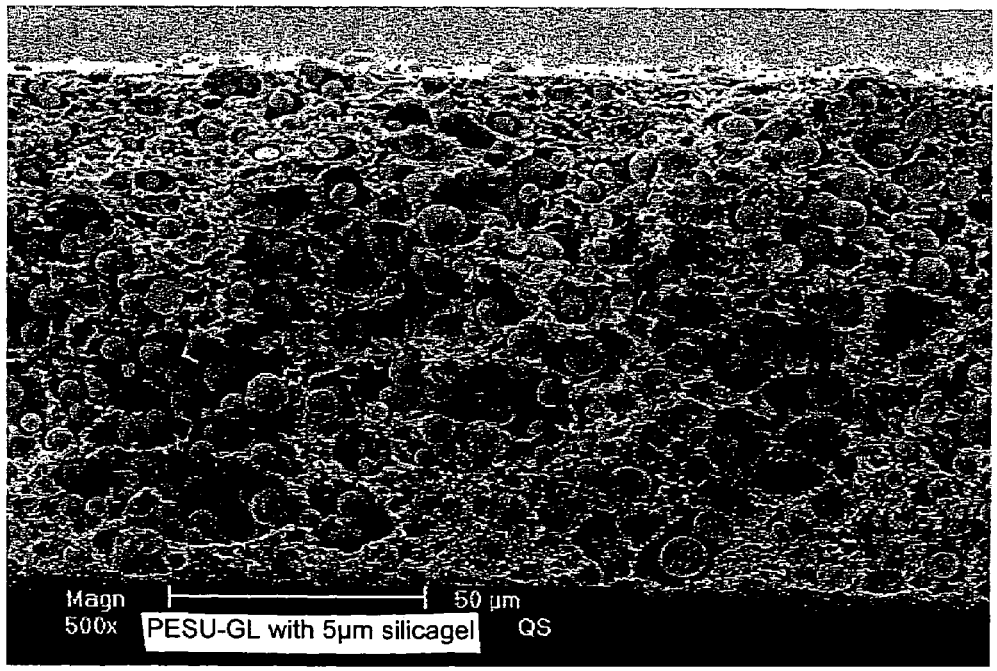
FIG. 2 shows a scanning electron micrograph of a cross section through an inventive adsorption membrane which has a symmetrical pore structure, with the adsorbent particles arranged essentially uniformly over the entire cross section of the membrane.
Figure 3:
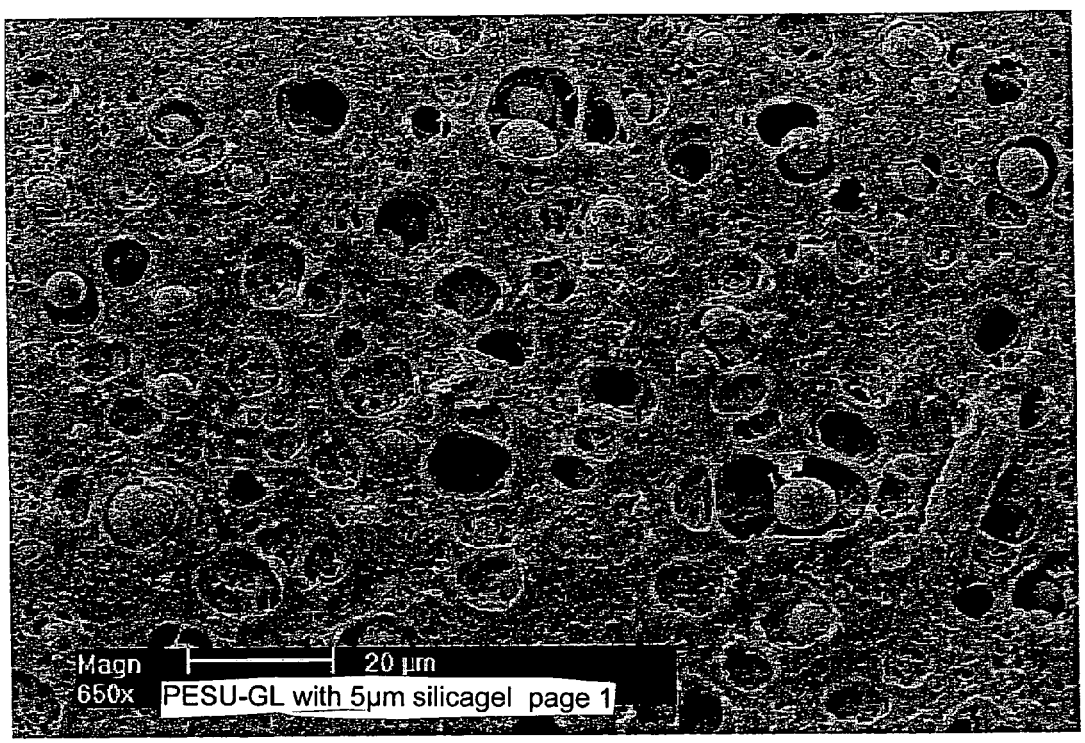
FIG. 3 shows a scanning electron micrograph, which is a view of an inventive adsorption membrane. It does not have a skin but instead has an essentially homogeneous pore structure.

As can be seen on the basis of FIG. 2 and FIG. 3, through the controlled phase reversal in the inventive method for producing an absorption membrane, the targeted adjustment of the ratio of precipitant and solvent for the polymer used prevents a sudden phase reversal from occurring when using a pure precipitant such as water, which would result in formation of a skin on the resulting membrane which would have only a few very small pores or none at all with an asymmetrical pore structure being formed in the corresponding membrane beneath that. Accordingly, an adsorption membrane produced by the inventive method does not have any skin (see FIG. 3) and also has a symmetrical pore structure (see FIG. 2). In addition, the adsorbent particles incorporated into the pores are distributed uniformly over the entire cross section of the inventive adsorption membrane and are essentially freely accessible, which ensures a high separation efficiency.

Figure 4:
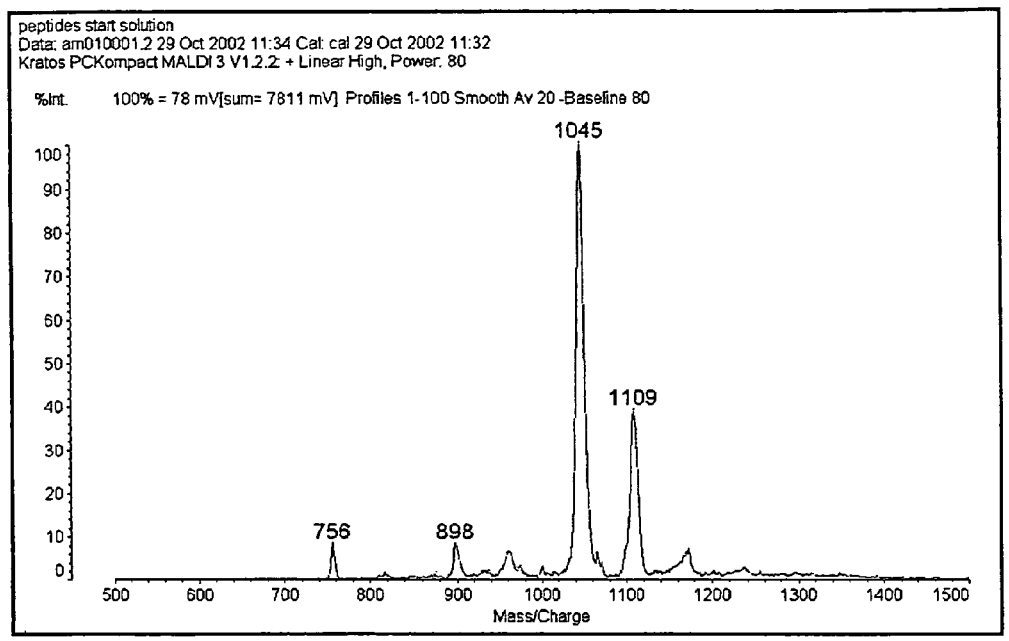
Figure 5:
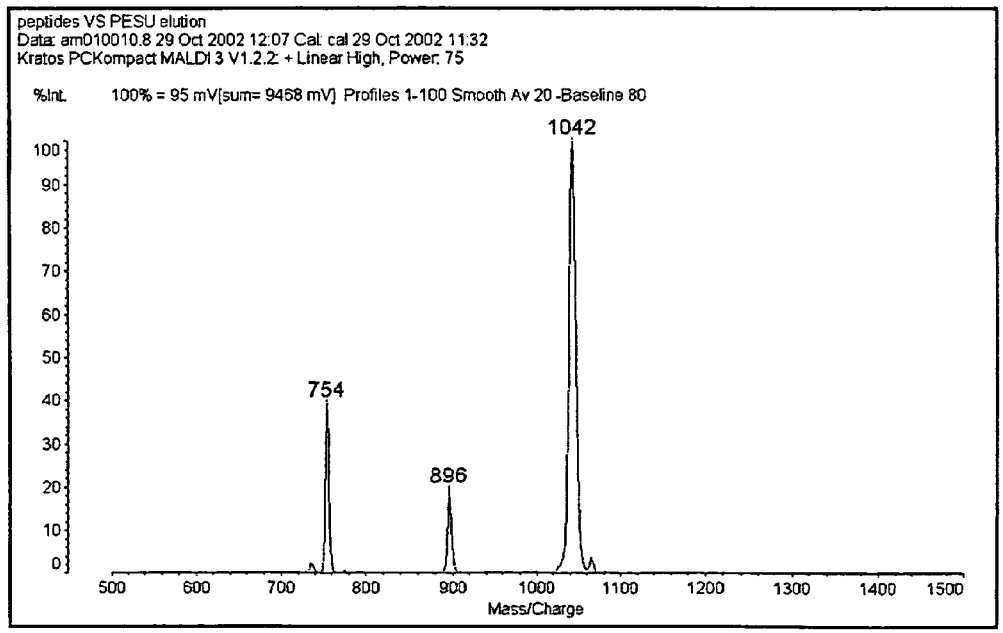
Figure 6:
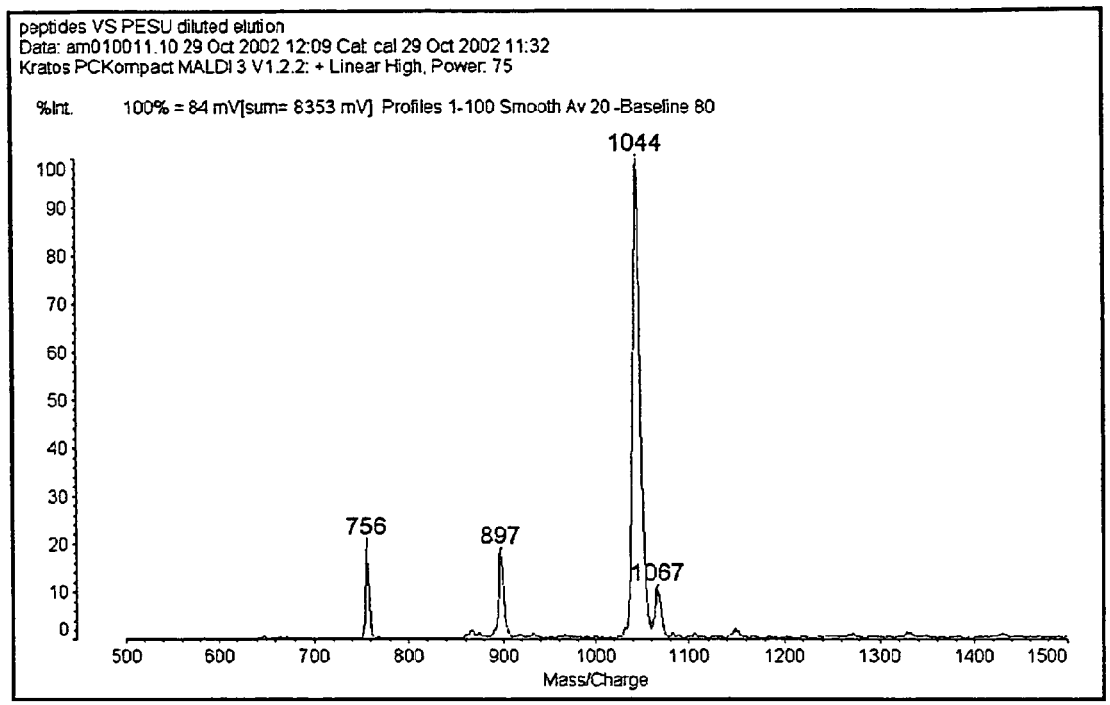

FIG. 4 through FIG. 6 show mass spectra of starting samples and samples concentrated and/or purified according to this invention.

DETAILED DESCRIPTION OF THE PREFERRED EMBODIMENTS

The present invention will now be explained in greater detail through the following nonrestrictive examples.

EXAMPLES

Abbreviations used:
ACN acetonitrile
BCA bicinchonic acid
BUDGE butanediol diglycidyl ether
CDI carboxydiimide
Cyt c cytochrome c
FAD flavine-adenosine dinucleotide
fm femtomole
HCl hydrochloric acid
IgG immunoglobulin G
Kpi potassium phosphate buffer
MALDI matrix assisted laser desorption ionization
MW molecular weight
NaCl sodium chloride
$NaCNBH_3$ sodium cyanoborohydride
NaOH sodium hydroxide
PBS phosphate-buffered saline
pg picogram
pm picomole
SKF gravity filtration
TFA trifluoroacetic acid
TOF MS time of flight mass spectrometry Unless otherwise indicated, deionized, i.e., demineralized, water has been used in all examples. Unless otherwise indicated, all centrifugation steps were performed in a K2S centrifuge from the Hettich Company with an oscillation rotor at 3000 rpm for five minutes at 22° C.

Agitation, unless otherwise indicated, was performed in all examples on a model DSG 304 agitator platform from the Heidolph Company at approx. 400 rpm at ambient temperature.

Example 1

Production of Irregularly Shaped Agarose Particles

Commercially available agarose from SIGMA Deisenhofen (order number A-6013, lot number 22K 0081) in the amount of 4 g was suspended in 100 mL water and dissolved in a boiling water bath. The solution was cast on a steel plate to form a layer 5 mm thick. After cooling and solidifying, the plate was divided into four parts. In a glass dish, 200 mL of a solution of 15% BUDGE and 10% 1 N NaOH in water was added to the parts and agitated for five hours at 50 rpm at ambient temperature. The plates were soaked in running tap water for three hours, then stored in water at 4° C. To detect the stabilization of agarose due to crosslinking, approx. 5 g was boiled for ten minutes with 5 mL water in a test tube, during which the piece of agarose retained its shape, i.e., the agarose did not go into solution.

The plates were divided into pieces approx. 2 cm in size and were transferred to a glass bottle together with 200 mL water. The pieces were treated for 30 minutes in an Ultraturrax homogenizer, model T25, from Janke and Kunkel at the highest setting (approx. 24,000 revolutions per minute) with water cooling. The resulting gel was placed in 80 mL Falcon tubes and was centrifuged for five minutes at ambient temperature in a laboratory centrifuge. The supernatant was decanted and an equal amount of water was added to the tubes. The gel was resuspended and centrifuged at 1,000 rpm for five minutes at ambient temperature. This procedure was repeated two more times. The supernatants thus obtained were combined, placed in 10 mL disposable plastic centrifuge tubes and centrifuged at 3000 rpm for ten minutes at ambient temperature in a laboratory centrifuge. The supernatant was decanted and an equal amount of water was added to the sediments in the tubes so that the gel was slurried again, combined and centrifuged as described above. This gave a yield of approximately 25 mL gel. The entire procedure was repeated at least three times and the resulting gels were combined. One drop of this gel was placed in a Neubauer counting chamber and inspected visually under the microscope at 40× magnification. Mainly particles in the size range from 5 μm to 25 μm were found. In addition, there were a few larger particles.

Example 2

Producing a CDI-Activated Gel

Packed, sedimented gel from Example 1 in the amount of 10 mL was treated twice each with a 25%, 50% and 75% solution of acetone in water, then slurried twice with anhydrous acetone and centrifuged after five minutes. Carbonyldiimidazole (CDI, 1 g) from Fluka, Buchs, Switzerland (order no. 21860, lot number 36208 1187) was dissolved in approx. 15 mL acetone and added to the gel. This mixture was agitated at 400 rpm for one hour at room temperature, then centrifuged and washed again twice with acetone and centrifuged. The activated gel was stored in anhydrous acetone at 4° C.

Example 3

Producing an Aldehyde-Activated Gel

Approximately 14 g moist sedimented gel from Example 1 was mixed with 14 mL water and 0.5 g sodium metaperiodate from Merck Darmstadt (order no. 106596, lot no. K23404696 726) and agitated at ambient temperature. After two hours, 50 mL water was added to the gel and centrifuged. The supernatant was decanted and 65 mL more water was added to the gel and the gel was slurried. After ten minutes it was centrifuged. To 1 mL Schiffs reagent from Merck Darmstadt (order no. 109034, lot no. 840296703) was added 0.1 mL of the packed gel and left to stand at ambient temperature. After 30 minutes, the gel had turned purple, indicating the presence of aldehyde groups.

Example 4

Converting the activated gels to a casting solution for producing polyether sulfone membranes Portions of 3 mL of the gels from Examples 2 and 3 were mixed with 10 mL of the casting solution and agitated for two hours at ambient temperature. After centrifuging at 3000 rpm for ten minutes, the supernatant was decanted and 50 mL acetone was added to the CDI-activated gel, and 50 mL water was added to the aldehyde-activated gel. After slurrying and leaving to stand for ten minutes, centrifugation was performed as described above. This procedure was repeated 4 more times. A solution of 10 mg/mL in water was prepared from each solution of the proteins cyctochrome c and ferritin. Of this, 0.5 mL portions were placed in small test tubes. Then 200 μL packed gel from Examples 2 and 3 was added to each. At the same time, 200 μL aliquots of the gels from Examples 2 and 3 which had not been treated with casting solution were added to the protein solutions. The mixtures were left to stand for 17 hours at ambient temperature. Then they were centrifuged, washed with 2 mL water and centrifuged again. This procedure was repeated four more times. In a visual inspection of the color intensity of the gels, no significant difference was found between the gels which were in contact with the casting solution and those which were not in contact with the casting solution. Accordingly, the casting solution did not have any negative effect on the chemical bonding capacity of the gels used.

Example 5

Coupling of Proteins to CDI-Activated Gels

Portions of 2-3 mL each of the packed gel from Example 2 were washed with cold water at 5° C. while centrifuging and placed in test tubes. Immediately thereafter, 3 mL to 5 mL of the following substances was added in a concentration of 10 mg/mL in water for each: cytochrome c (order no. C-2506, lot no. 110K7049) and FAD (order no. F-6625, lot no. 30K0628), both from SIGMA Deisenhofen and ferritin from SERVA Heidelberg (order no. 21318, control D). The mixtures were agitated for 17 hours at ambient temperature. The gels were washed three times with water and centrifuged. Then they were washed 4 times with a solution of 1 M NaCl in 0.01 M Kpi, pH 7.0. The supernatants were then colorless. However there was a definite coloration of the gels due to the chemically bound cyctochrome c, FAD and ferritin.

Example 6

Coupling of Protein A to Aldehyde-Activated Gels

To 25 mL aldehyde-activated gel from Example 3 was added 100 mg protein A from RepliGen (lot RN020759) dissolved in 2 mL PBS and 8 mL 1 M Kpi, pH 8.0, and the mixture was agitated for three hours at room temperature. Then the supernatants were centrifuged for fifteen minutes, the gel was washed with 1 M NaCl in 10 mM Kpi, pH 7.0, 30 mg NaCNBH$_3$ was added and the mixture was agitated for ten minutes. Then the gel was agitated for five minutes in 25 mL portions of each of the following solutions:

1 M NaCl in 10 mM Kpi, pH 7;
1 mM HCl in deionized water;
1 M NaCl in 10 mM Kpi pH 7;
100 mM glycine/HCl pH 2.8;
1 M NaCl in 10 mM Kpi pH 7;
1 mM NaOH in deionized water;
1 M NaCl in 10 mM Kpi pH 7.

Between each treatment, the gel was centrifuged for fifteen minutes. Then the gel was stored at 4° C. in 1 M NaCl.

Detection of coupling of protein A to the gel and detection of binding of IgG to the coupled protein A:

BCA Test:

Approximately 50 mg sedimented gel was weighed into a test tube and agitated for one hour at ambient temperature together with 2 mL BCA reagent from PIERCE Chemicals, Rockford, Ill. USA. Due to the reduction of the copper ions present in the reagent together with the bicinchonic acid, this yields a colored complex, the intensity of which is proportional to the quantity of protein present. The gel was centrifuged for 10 minutes after a reaction time of 60 minutes and the supernatant was measured at a wavelength of E 562 nm in a spectrophotometer. On the basis of a standard solution of protein A in PBS with a known concentration, the amount of protein originally on the gel was determined.

Binding of IgG:

Sedimented gel in the amount of 1 g was washed twice with 2 mL PBS, agitated for approx. 25 minutes with 2 mL human plasma that had been diluted 1:20 with PBS and then washed 4 times with 2 nL PBS. Then the bound IgG was eluted with 2 mL of a solution of 0.1 M glycine/HCl, pH=2.8, for fifteen minutes. The supernatant was measured at 280 nm against the eluent using a spectrophotometer. A solution of 1 mg/mL IgG yielded a distinction of 1.1 at 280 nm in a layer thickness of 1 cm.

The results are summarized in the following table.

TABLE 1

Coupling efficiency for protein A and binding capacity for IgG of the inventive gel from Example 6.

| Sample | BCA Test | | | Binding of IgG | |
|---|---|---|---|---|---|
| Gel | E 592 nm | µg/mL gel | mL | E 280 nm | µg/mL gel |
| Weight 52.4 mg | 0.311 | 533 | 1.8 | 0.208 | 340 |

Example 7

Converting an Aldehyde-Activated Gel to a Non-Aqueous Phase

Gel from Example 6 in the amount of 25 mL was centrifuged for fifteen minutes and washed with PBS for five minutes. The gel was centrifuged and agitated for fifteen minutes with 25 mL 25% 2-pyrrolidone in PBS, centrifuged and agitated for fifteen minutes with 50% 2-pyrrolidone in PBS, centrifuged and agitated with 100% 2-pyrrolidone for fifteen minutes and then centrifuged. This last step was repeated and the gel was stored at 4° C.

Example 8

Producing a Microporous Polyether Sulfone Membrane Containing Agarose Coupled to Protein A as a Filler A casting solution having the following composition was prepared: 81.8% 2-pyrrolidone, 11.5% polyether sulfone E6020, 4.7% water and 2% glycerol (86.5%) were dissolved at 50° C. while stirring for 8 hours. A mixture of 90% of this solution and 10% of protein A reacted agarose from Example 6 was prepared [by agitating] at 30° C. for 30 minutes using a propeller stirrer at 600 rpm. In addition, this casting solution was degassed in a vacuum of 150 mbar for 24 hours. This degassed casting solution was shaped by means of a drawing device in an aqueous precipitation bath to form a microporous membrane with a thickness of 150 µm. After obtaining approximately 1000 cm² of a microporous structure, the piece of membrane was washed with PBS and stored in PBS at 4° C.

Example 9

Binding of IgG to an Inventive Membrane Containing Filler

Six filter rounds from Example 8 having a diameter of 25 mm were installed in a filtration unit (order no. 16517 from the Sartorius Company (referred to here as PCV)) and the following solutions were filtered through the membranes by using an attached 10 mL disposable syringe and gravity filtration (abbreviated here as SKF):

10 mL 1×PBS; 10 mL humanplasma diluted 1:20 in PBS; 10 mLPBS.

The bound IgG was eluted with 3 mL of a solution of 0.1 M glycine/HCl, pH=2.8.

Pieces of the membrane from Example 8 (10 cm² or 20 cm²) were agitated for the stated periods of time with 10 mL of the following solutions each in a petri dish: 15 min with 10 mL PBS; 1.5 h with 10 mL human plasma 1:20 in PBS; 2×15 min with 10 mL PBS. Elution was performed by agitating for 2 hours in 3 mL 0.1 M glycine/HCl, pH=2.8. This experimental setup is referred to below as the shake test.

The supernatants from both experiments were measured against the eluent at 280 nm in a spectrophotometer. A solution of 1 mg/mL IgG yielded an extinction of 1.1 at 280 nm with a layer thickness of 1 cm.

The results are summarized in Table 2.

TABLE 2

| | Binding of IgG | | |
|---|---|---|---|
| Sample | mL | E 280 nm | µg/cm² |
| SKF in PCV | 2.9 | 0.129 | 18 |
| 6-layer 18.6 cm² | 4 | 0.095 | 19 |
| Shake test 10 cm² | 3 | 0.031 | 9 |
| Shake test 20 cm² | 3 | 0.033 | 5 |

These results show a binding of IgG to the inventive membrane.

Example 10

Production of a Microporous Polyether Sulfone Membrane Loaded with Hydrophobic Ligands Containing Silica Particles as Filler A casting solution having the following composition was prepared: 81.8% 2-pyrrolidone, 11.5% polyether sulfone E6020, 4.7% water and 2% glycerol (86.5%) were dissolved while stirring at 50° C. for eight hours. A mixture of 90% of this solution and 10% of a silicic acid material containing $C_{18}$ ligands from the company Merck in Darmstadt (order no. 1.116177, lot L448077 234) was prepared by agitating at 600 rpm for 30 minutes at 30° C. using a propeller stirrer. In addition, this casting solution was degassed for 24 hours in a vacuum of 150 mbar. This degassed casting solution was shaped to yield a microporous membrane with a thickness of 150 µm by means of a drawing device in an aqueous precipitation bath. After obtaining approx. 1000 cm² of a microporous structure, the piece of membrane was washed with PBS and stored at 4° C. in PBS.

Example 11

Manufacturing Centrifugal Units with the Inventive Membrane from Example 10

Filter rounds 3 mm in diameter made of an inventive membrane from example 10 were installed in centrifugal units developed as experimental products bearing the name Microspin Columns by the company Vivascience AG, Hannover and were secured by a well-fitting insert. The units had an effective filter area of 3.1 mm². The units are referred to below as RP-18 Microspins.

Example 12

Concentrating Bioactive Peptides with RP-18 Microspins

The following bioactive peptides were obtained from SIGMA Deisenhofen:

Bradykinin fragments 1-7 (order no. B-1651, lot no. 41K13641)

Angiotensin II fragments 1-7 (order no. A-9202, lot no. 21K5122)

Angiotensin II (order no. A-9525, lot no. 31K51144)

These are listed in tabular form in Table 3.

TABLE 3

Molecular weights and amounts of the bioactive peptides used.

| Designation | MW | Total Amount | | 1:10 | |
|---|---|---|---|---|---|
| Bradykinin fragments 1-7 | 757 Da* | 12 pg | 16 pmol | 1.2 pg | 1.6 pmol |
| Angiotensin II fragments 1-7 | 899 Da | 9 pg | 10 pmol | 0.9 pg | 1.0 pmol |
| Angiotensin II | 1046 Da | 10 pg | 10 pmol | 1.0 pg | 1.0 pmol |

*Dalton

A solution of bradykinin fragments 1-7 (1600 fmol/µL), angiotensin 11 fragments 1-7 (1000 fmol/µL) and angiotensin II (1000 fmol/µL) in 0.1% TFA in deionized water was prepared (referred to here as undiluted starting solution). In addition, a 1:10 dilution of the above solution of peptides in 0.1% TFA was prepared (referred to here as starting solution diluted 1:10). These two mixtures constituted the starting solutions for the following experiments. 2 µL of each solution was pipetted onto a MALDI target and dried at ambient temperature (dried droplet method).

Acetonitrile (100%, 100 µL) was pipetted into RP-18 Microspins and the installed membranes were washed by centrifugation for one minute at 2000 rpm. The flow-through was discarded.

The membranes were equilibrated by centrifugation for one minute at 2000 rpm with 100 µL 0.1% aqueous TFA solution. The flow-through was discarded and this step was repeated.

Undiluted starting solution in 10 µL portions and the starting solution diluted 1:10 were pipetted directly onto the membrane and centrifuged for one minute at 2000 rpm. The flow-through was pipetted onto a MALDI target and dried for five minutes at ambient temperature.

The membranes were washed by centrifugation for one minute at 2000 rpm with 20 µL 0.1% TFA. The flow-through was discarded and this step was repeated. Then the membranes were dried by centrifugation for one minute at 13,000 rpm. Four µL portions each of a solution of 10 mg/mL α-cyano-4-hydroxycinnamic acid in 50% ACN and 0.1% TFA was pipetted onto the membrane and then centrifuged first for one minute at 2000 rpm and then for one minute at 13,000 rpm. This resulted in the peptides retained by the membrane being desalinated, concentrated and eluted.

The following samples were pipetted onto MALDI targets and dried for five minutes at ambient temperature:

1 the undiluted starting solution (2 µL)
2 the starting solution diluted 1:10 (2 µL)
3 the flow-through of the load of undiluted starting solution (2 µL)
4 the total eluate of the undiluted starting solution (4 µL)
5 the total eluate of the starting solution diluted 1:10 (4 µL)

The samples were then measured using an analytical III MALDI TOF MS device from Kratos/Shimadzu. Those skilled in the art are familiar with the operation of such instruments which thus constitute the state of the art.

The spectra thus obtained are shown in FIG. 4 through FIG. 6.

FIG. 4 shows the spectrum of the undiluted starting solution.

The signals are to be assigned to the following peptides: bradykinin fragments 1-7=756 m/z, angiotensin II fragments 1-7=898 m/z and angiotensin II=1045 m/z.

No signals could be detected with the starting solution diluted 1:10 and thus no analyzable spectrum could be obtained.

FIG. 5 shows the spectrum of the bioactive peptides after concentrating and desalinating through RP-18 Microspins from Vivascience AG after elution. The three peptides used can be identified unambiguously on the basis of their atomic number. No peptides could be detected in the flow-through. Accordingly, the totality of the available amount of bioactive peptides was retained by the membrane.

FIG. 6 shows the spectrum of the bioactive peptides of the starting solution diluted 1:10 after concentrating and desalinating through RP-18 Microspins from Vivascience AG after elution. The three peptides used were identified unambiguously on the basis of their atomic number in contrast with direct analysis of the corresponding starting solution, as described above. No peptides could be detected in the flow-through. Accordingly the totality of the available amount of bioactive peptides was retained by the membrane.

It has thus been demonstrated that with the help of preparation of the sample with RP-18 Microspins, bioactive peptides can be concentrated. In contrast with direct MALDI analysis of the 1:10 diluted starting solution, these samples could be detected successfully after treatment with the RP-18 Microspins.

What is claimed is:

1. Adsorption membrane comprising a microporous polymer membrane having an essentially symmetrical pore structure, with adsorbent particles which are arranged essentially uniformly over the entire cross section of the membrane and have either a spherical or an irregular shape being incorporated into the pores,
   wherein the adsorbent particles are agarose particles modified with a ligand, and
   wherein the adsorption membrane is produced by a method comprising the following steps:
   (a) Producing a polymer casting solution,
   (b) Introducing modified adsorbent particles into the polymer casting solution,
   (c) Bringing the resulting solution into a membrane shape,
   (d) Introducing the shaped solution into a precipitation bath to carry out a controlled phase reversal to form a porous membrane filled with particles and
   (e) Removing the remaining solvent.

2. Adsorption membrane as claimed in claim 1 wherein the membrane has a thickness of 50 µm to 500 µm.

3. Adsorption membrane as claimed in claim 1 or 2 wherein the pores have a maximum diameter of 0.1 µm to 10 µm.

4. Adsorption membrane as claimed in claim 1, wherein the adsorbent particles have a diameter 5% to 80% smaller than the maximum pore diameter.

5. Adsorption membrane as claimed in claim 1, wherein the particles are either monodisperse or have a continuous particle size distribution.

6. Adsorption membrane as claimed in claim 1, wherein the amount by weight of the adsorbent particles is 1 to 70%, based on the total membrane.

7. Adsorption membrane as claimed in claim 1, wherein between 10% and 80% of the pore volume of the microporous polymer membrane is filled with adsorbent particles.

8. Adsorption membrane as claimed in claim 1, wherein the microporous polymer membrane comprises at least one polymer selected from the group consisting of polysulfone, polyether sulfone, cellulose acetate, cellulose acetate butyrate, acrylonitrile-PVC copolymer, polyvinylidene fluoride, polystyrene, polystyrene-acrylonitrile copolymer, polyolefins and polyamides.

9. Adsorption membrane as claimed in claim 1 wherein the ligand is protein A.

10. Method of producing an adsorption membrane comprising a microporous polymer membrane having an essentially symmetrical pore structure, wherein adsorbent particles are incorporated into the pores which particles are arranged essentially uniformly over the entire cross section of the membrane and have either a spherical or an irregular shape, wherein the adsorbent particles are agarose particles modified with a ligand, wherein the method comprises the following steps:
  (a) Producing a polymer casting solution,
  (b) Introducing modified adsorbent particles into the polymer casting solution,
  (c) Bringing the resulting solution into a membrane shape,
  (d) Introducing the shaped solution into a precipitation bath to carry out a controlled phase reversal to form a porous membrane filled with particles and
  (e) Removing the remaining solvent.

11. Method as claimed in claim 10, wherein the controlled phase reversal is performed through targeted adjustment of the ratio of precipitant and solvent for the polymer used.

12. Adsorber device comprising a housing which defines a volume, wherein the housing has a first open end and a second open end at a distance from the first open end and an adsorption membrane as claimed in claim 1 is arranged in a section of the volume.

13. Adsorber device as claimed in claim 12, wherein the adsorption membrane is arranged directly on one of the two ends of the housing.

14. Centrifuge tube comprising an adsorber device as claimed in claim 12 or 13.

15. Multiple microtiter plate comprising adsorber devices arranged side by side as claimed in claim 12 or 13.

* * * * *